US00PP14424P39

(12) United States Plant Patent
Strickland

(10) Patent No.: US PP14,424 P3
(45) Date of Patent: Dec. 30, 2003

(54) OAK TREE NAMED 'QSFTC'

(50) Latin Name: *Quercus sp.*
Varietal Denomination: QSFTC

(75) Inventor: Thomas Julian Strickland, Statesboro, GA (US)

(73) Assignee: Tree Introductions, Inc., Bishop, GA (US)

( * ) Notice: Subject to any disclaimer, the term of this patent is extended or adjusted under 35 U.S.C. 154(b) by 0 days.

(21) Appl. No.: 10/126,235

(22) Filed: Apr. 17, 2002

(65) Prior Publication Data

US 2003/0200587 P1 Oct. 23, 2003

(51) Int. Cl.[7] ..... A01H 5/00
(52) U.S. Cl. ..... Plt./225
(58) Field of Search ..... Plt./225

(56) References Cited

U.S. PATENT DOCUMENTS

PP4,149 P * 11/1977 Schmidt, III ..... Plt./225
PP13,524 P3 * 1/2003 Strickland ..... Plt./225

OTHER PUBLICATIONS http://hort.ifas.ufl.edu/trees/QUESHUA.pdf.*
http://hort.ifas.ufl.edu/trees/quenuta.pdf.*

* cited by examiner

*Primary Examiner*—Bruce R. Campell
*Assistant Examiner*—W C Haas
(74) *Attorney, Agent, or Firm*—Klarquist Sparkman LLP

(57) ABSTRACT

An Oak tree named 'QSFTC' having a dense, upright, uniform branching pattern, glossy, dark green leaf, and red fall color, and also which is capable of being reproduced reliably using vegetative cuttings.

6 Drawing Sheets

Latin name of the genus and species of the plant claimed: Quercus sp.
Variety denomination: 'QSFTC'.

BACKGROUND OF THE INVENTION

The present invention relates to a new and distinct variety of Quercus plant, which has been given the varietal name 'QSFTC'. I discovered my new tree in 1995 as a chance seedling in a cultivated area of a nursery growing area in Bulloch County, Ga.

The parentage of this tree is not totally certain. It is definitely a red oak type usually represented by Pin Oak, *Quercus palustris*, or Red Oak, *Quercus rubra*. There are also several related species, including Nuttall Oak (*Quercus nuttallii*), Shumard Oak (*Quercus shumardii*), and Scarlet Oak (*Quercus coccinea*). My new tree has characteristics and a history that have prevented making an exact identification of its species possible. However, I believe it is a new variety of *Quercus shumardii.*

Seeds were collected from a group of three trees of an unknown variety in Birmingham, Ala. The seed were collected in fall of 1991 and planted into seedbeds in late winter of 1992. In spring of 1993, 1,200 bare-root liners were transplanted to a growing area of a nursery. This is where I discovered my new variety as a single plant. The original tree has remained at this location since its discovery.

The original tree has displayed characteristics resembling Nuttall Oak and Scarlet Oak, as well as, Shumard Oak. There is much confusion over the exact identification of this tree, and several experienced individuals have expressed differing opinions. The only consistency has been the opinion that the acorn is generally the most distinguishing characteristic determining the species difference between Nuttall Oak and Shumard Oak. Other trees from the group of 1,200 have fruited, and their acorns resemble both Nuttall Oak and Shumard Oak. However, acorns from my new tree have more characteristics of a Shumard Oak which suggests that my new tree is most likely a Shumard Oak or at least has Shumard Oak as a parent. Other physical characteristics of the tree, such as leaf size, sinus depth, or bud features, do not provide definitive answers as to the true parentage of the tree.

Also, Shumard Oak, as well as most other red oak types, readily hybridize with one another, and thus there is a possibility that this tree is a result of a cross between a Nuttall Oak and Shumard Oak or some other species of red oak. In Texas, Nuttall Oak is found in the lower Southeast corner of Texas, Shumard is located in a wide band covering most of the eastern part of the state, and Texas Red Oak, *Quercus texana*, is the primary tree in the central part of the state east of Dallas. There is also a large swath of habitat between the primary Shumard Oak and Texas Red Oak regions where the predominant tree is a hybrid between Shumard Oak and Texas Red Oak. Thus, hybrids are common and can easily make up a large population of the trees in any given area.

In 1995, this original tree of my new variety was successfully propagated by softwood cuttings at my direction, and the progeny have thus far proven to retain the dense, upright, uniform branching pattern, glossy, dark green leaf, and red fall color of the original tree even as smaller plants.

I have observed this original tree of my new variety and asexually propagated progeny for a period of time and believe my new variety particularly useful as a specimen or for grouping in lawns, parks, golf courses, commercial landscapes, and as a street tree. It provides good shade, has a fast growth rate, adapts well to various planting conditions, and has good structural integrity. It also provides ornamental interest with its red fall color.

Typical Shumard Oaks and Nuttall Oaks are pyramidal trees that become more spreading with age. My original tree and asexually propagated progeny have an upright shape. I expect the trees to become more spreading with age as is typical of the species. Both Shumard Oak and Nuttall Oak typically reach 40 to 60 feet high and wide in the landscape, but can reach 100 feet or more in nature.

My new variety has been asexually propagated at my direction in Bulloch County, Ga. from softwood cuttings. This propagation and observation of the resulting progeny have proven the characteristics of my new variety to be firmly fixed. Furthermore, these observations have confirmed that my new variety represents a new and improved variety of Shumard Oak as particularly evidenced by the dense, upright, uniform branching pattern, glossy, dark green leaf, and red fall color and which can reliably be asexually propagated using vegetative propagation techniques. The progeny have yet to produce any acorns.

BRIEF SUMMARY OF THE INVENTION

As I observed the original tree of my new variety, the uniqueness of this tree became apparent because of its dense, upright, uniform branching pattern, glossy, dark green leaf, and consistent red fall color. These characteristics distinguish my new tree from other Shumard Oaks of which I am aware. This tree is capable of being reproduced reliably using vegetative cuttings.

BRIEF DESCRIPTION OF THE DRAWING

The accompanying photographs depict the color of the tree and foliage of my new variety as nearly as is reasonably possible to make the same in a color illustration of this character. It should be noted that colors in a photograph can vary with lighting conditions. Also, growing conditions can affect plant color.

DETAILED BOTANICAL DESCRIPTION

Figure 1:
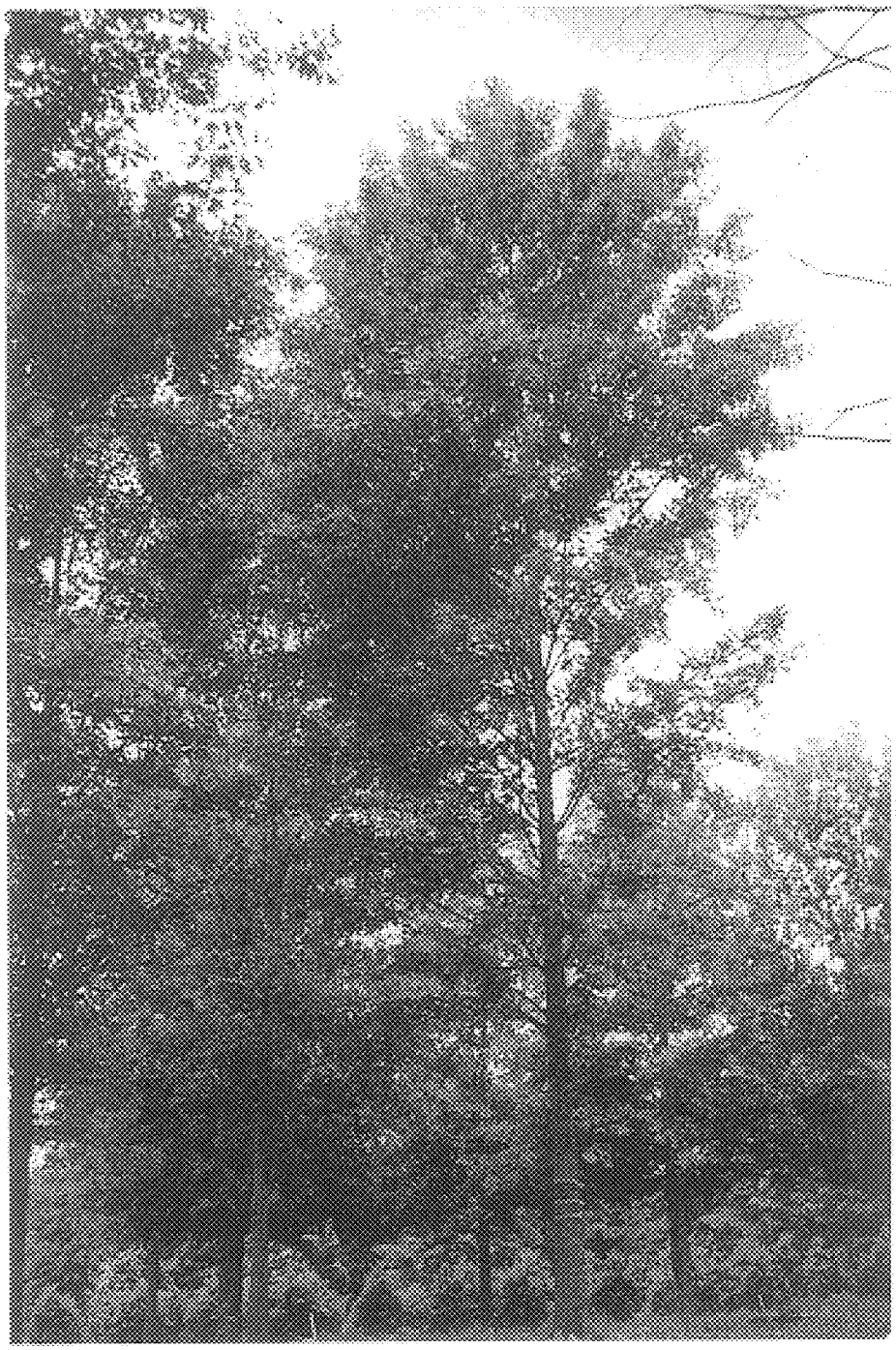
FIG. 1 is a photograph of the parent tree of my new variety in summer leaf.
Figure 2:
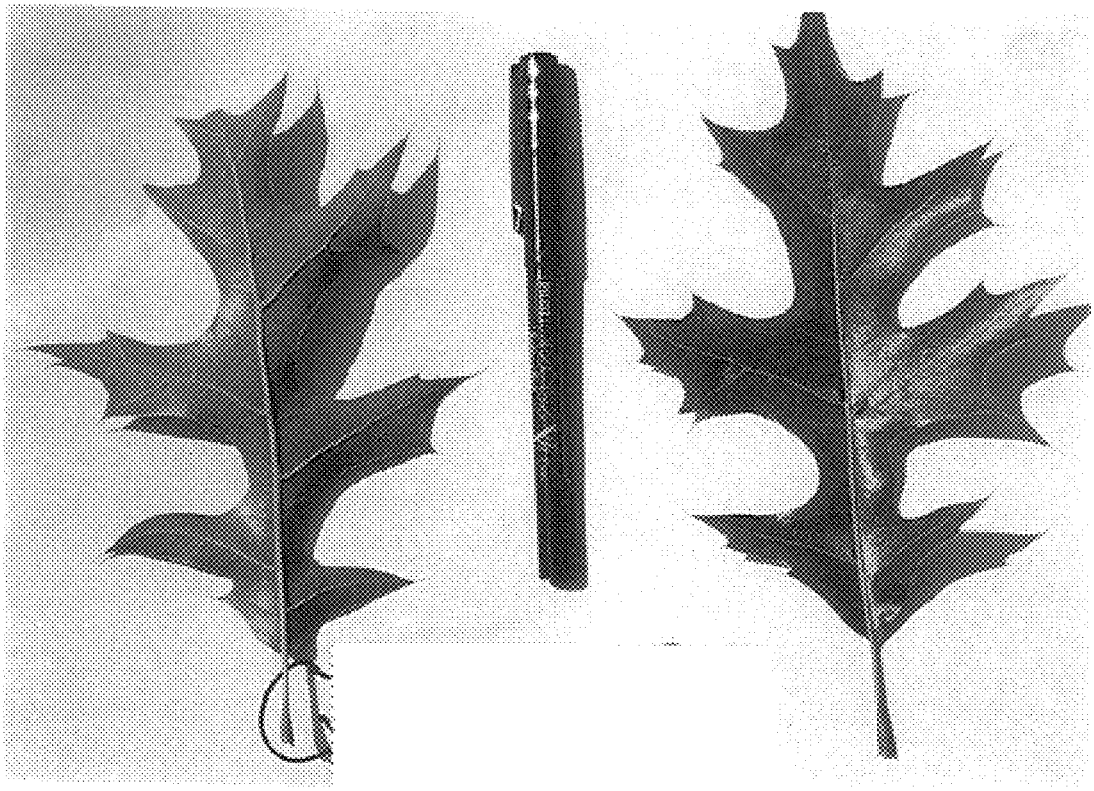
FIG. 2 is a close up photograph of two single leaves depicting the upper and under side of leaves from a tree of my new variety.
Figure 3:
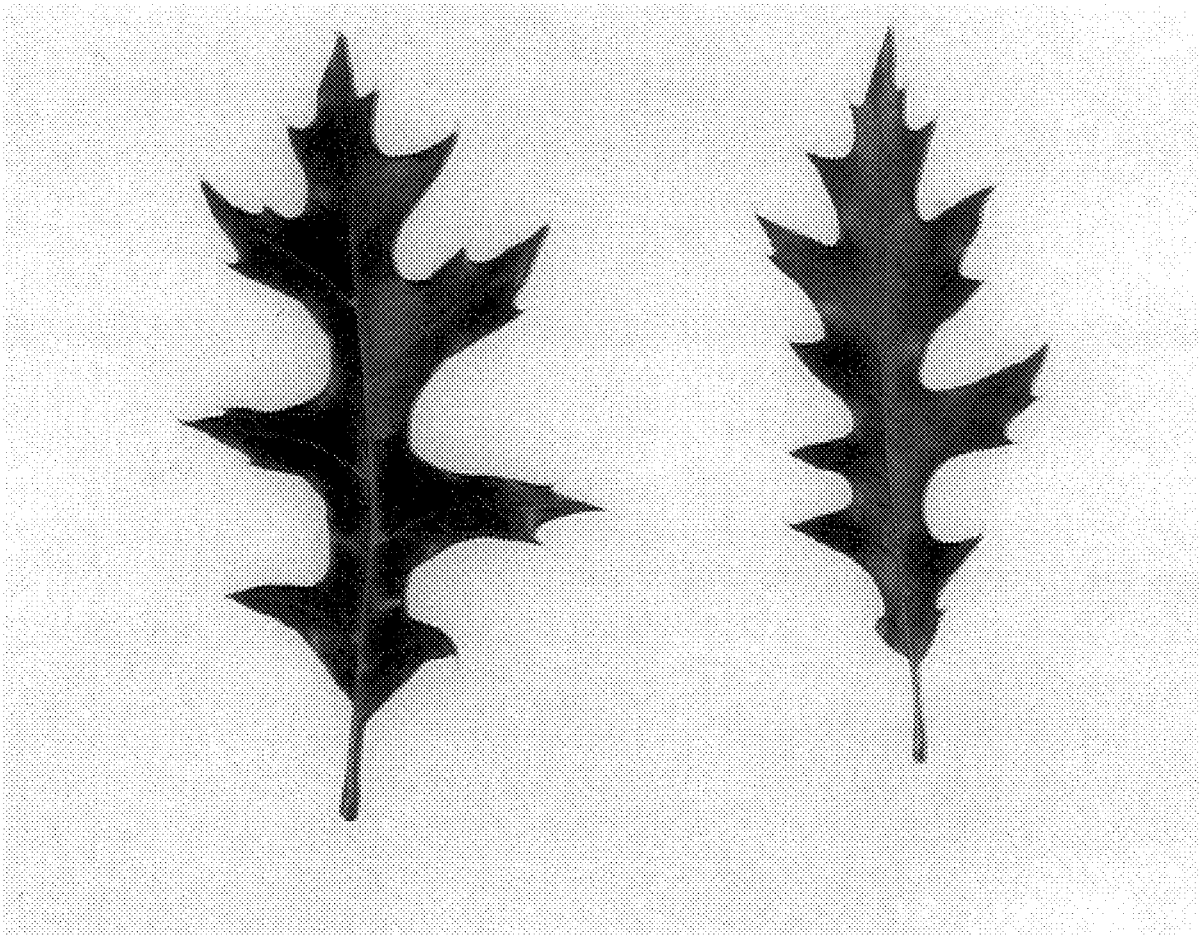
FIG. 3 is a close up photograph of my variety showing typical fall leaf color.
Figure 4:
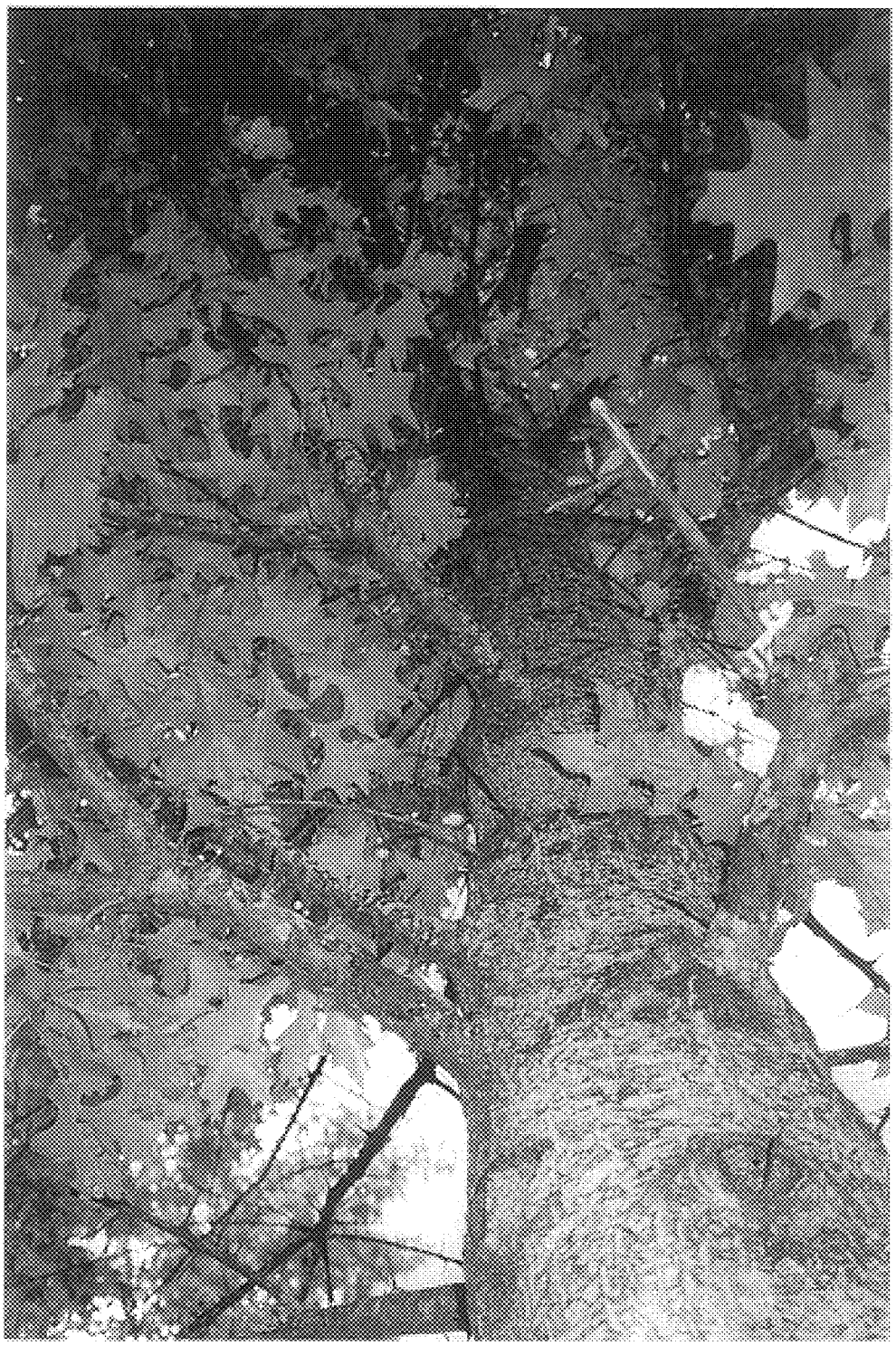
FIG. 4 is a close up photograph of a portion of the trunk of the original tree.
Figure 5:
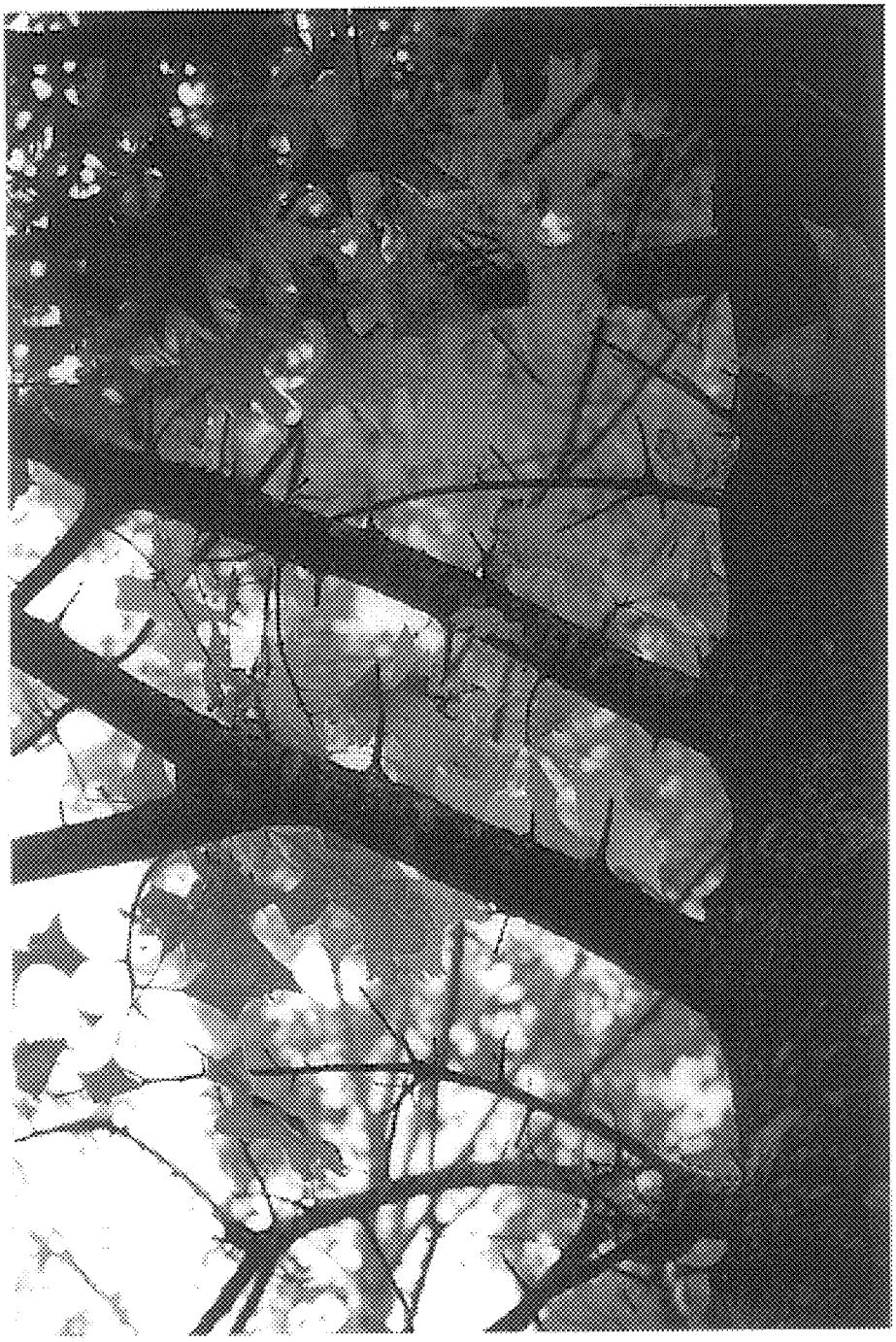
FIG. 5 is a photograph showing the typical branching angle of branches of my new variety from the main trunk.

The following detailed description of the 'QSFTC' variety is based on observations of the original tree, which was about nine years old and of about six year old progeny growing in typical outdoor conditions in Bulloch County, Ga. The progeny had been asexually propagated from softwood cuttings at my direction in 1995. The observed progeny have thus far proven to retain the dense, upright, uniform branching pattern, glossy, dark green leaf, and red fall color of the parent tree even as smaller plants.

Scientific name: Quercus sp., Varietal Name 'QSFTC'.

Parentage:

*Seed parent.*—Unknown.

*Pollen parent.*—Unknown. Believed to have *Quercus shumardii* as one of the parents.

Tree:

*Overall shape.*—Upright, more spreading with age, with a full head and central dominant leader.

*Height.*—About 38 feet.

*Width.*—About 24 feet.

*Caliper.*—Original tree, 9 inches at 12 inches above ground.

*Vigor.*—Fast growing; growth of 11 typical branches during 2001 growing season ranged from about 2 inches to about 15 inches.

*Trunk bar texture.*—In youth bark is smooth. Mature Bark: Develops shallow ridges and furrows.

*Trunk bark color.*—Light grey (RHS 201D).

*Patches or other markings.*—Greyed-Green; Color: (RHS 194C).

*Primary branches.*—Somewhat upright. Typical branches emerge from the trunk at 60 degree angle.

*Branch color.*—One year old branches, greyed-orange (RHS 164A).

*Branch pubescence.*—None observed.

*Branch lenticels.*—Greyed-orange (RHS 163D).

*Internode length.*—Eleven typical one year old branches during 2001 growing season ranged from about one-half inch to about two inches.

*Hardiness.*—Unknown, only observed in Zones 7 and 8 as of this time.

*Disease resistance.*—No susceptibility to diseases has been observed.

Leaves: The leaves of Nuttall Oak, Shumard Oak, Pin Oak, and Scarlet Oak all closely resemble one another, and my tree has leaves that most resemble a typical *Q. shumarii* in size and shape, however, some characteristics indicate that it could also be influenced by Scarlet Oak as well.

*Size and shape.*—Alternate, simple, obovate to elliptic, 4 to 8" long, 3 to 4" wide, with 7 to 9 pinnatifid lobes. Sinuses cut deeply to the midrib.

*Base.*—Acute.

*Apex.*—Acute.

*Margin.*—Spinose-lacerate, serrations between leaf points.

*Texture.*—Upper leaf: Smooth; Lower leaf: Smooth, somewhat rougher than upper surface.

*Sheen.*—Upper leaf: Glossy; Lower leaf: Dull.

*Petiole.*—1½ inch to 2¼ inch; Color: Yellow-green (RHS 146C).

*Stipules.*—None observed.

*Leaf color.*—Upper leaf surface: Dark glossy green (RHS 136A)(in summer), typically deep red (RHS 53B)(in fall). Lower leaf surface: Lighter green (RHS 146B)(in summer), typically deep red (RHS 53B) (in fall). Vein: Color: Yellow-green (RHS 146C).

*Pubescence.*—None observed.

The length, width, thickness and other measurements mentioned above were obtained from observations of about ten typical leaves in 2001.

Flowers: Most oaks have flowers so similar that it is difficult to distinguish between species based on flower type alone. The flowers of my new tree are typical of most oaks. The trees are monoecious. The staminate catkins are pendent and clustered. The individual flowers comprise 4- to 7-lobed calyx that encloses 6 to 12 stamens. Pistillate flowers are solitary or in few to many-flowered spikes from the axils of the new leaves. Individual pistillate flowers consist of a 6-lobed calyx surrounding the ovary, with the whole partly enclosed in an involucre.

*Buds.*—Imbricate, ¼ to ⅜" long, glabrous, light brown; (RHS 200D).

Fruit: (Observations from a limited number of typical acorns from the original tree, acorns have yet to be observed on progeny.)

Figure 6:
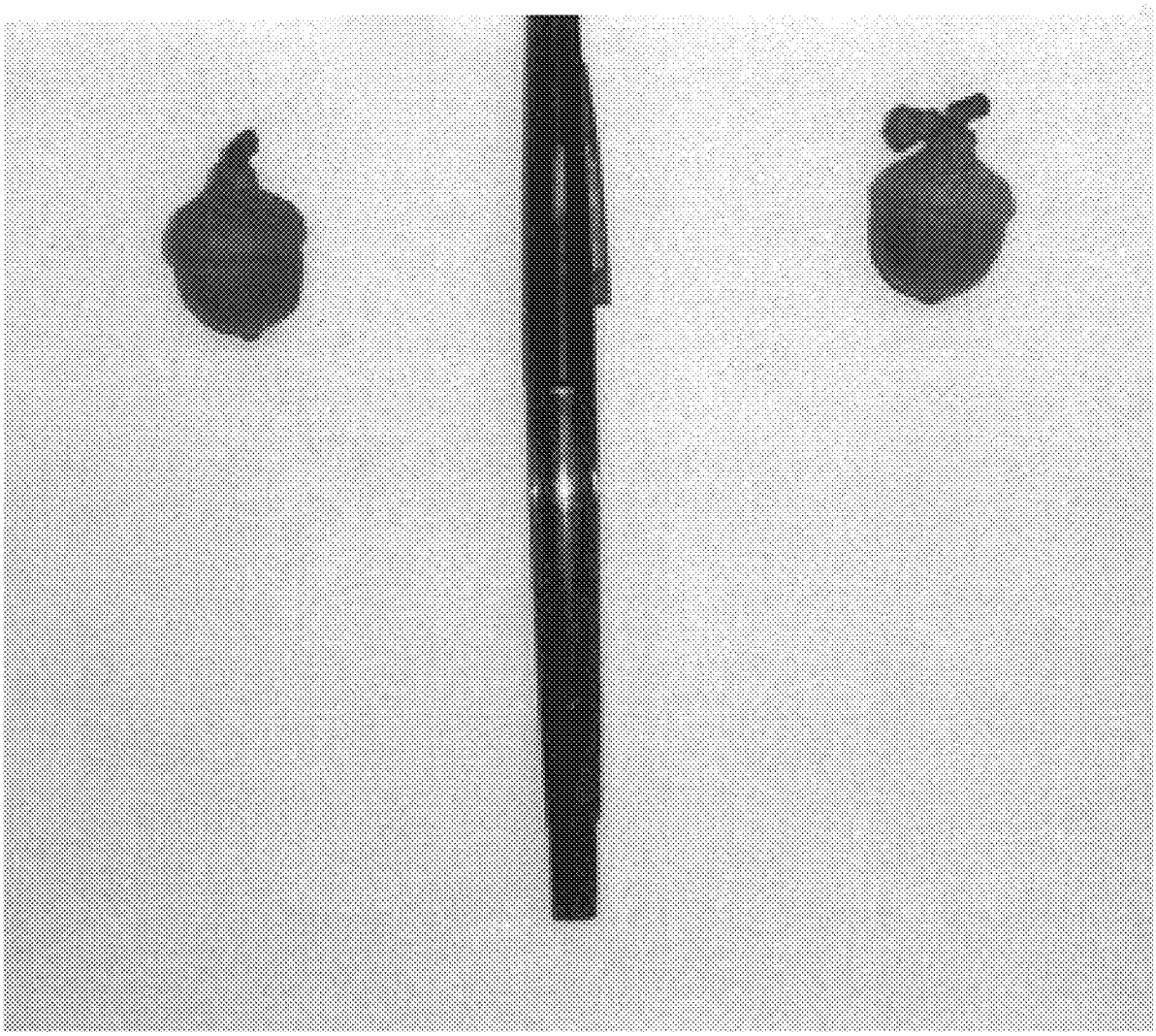
FIG. 6 is a close up photograph of typical acorns from the original tree of my new variety.

The acorn of this tree most closely resembles that of Shumard Oak. In this case, they are typical of the species. Acorns are ovate, ¾ to 1½" long, short-stalked, oblong-ovoid and covered only at the base by the cap (FIG. 6). The acorn is grayed-orange in color (RHS 177B) with dark brown (RHS 200A) striations. The cap is light brown (RHS 199B). The acorn is the best identifying feature to discriminate Shumard Oak from Nuttall Oak. Shumard Oak has an acorn of approximately the same size and shape, though sometimes Shumard acorns are more ovate, as Nutall Oak. However, in Shumard Oak, the cap covers only the top part of the acorn, and the striations are more pronounced.

I claim:

1. A new and distinct variety of Oak tree substantially as herein shown and described, characterized particularly as to novelty by its unique glossy, dark green leaf and its red fall color.

* * * * *